United States Patent
Krause et al.

(10) Patent No.: US 8,528,744 B2
(45) Date of Patent: Sep. 10, 2013

(54) HYDROPHILIC MEMBRANES WITH A NON-IONIC SURFACTANT

(75) Inventors: Bernd Krause, Rangendingen (DE); Markus Hornung, Nehren (DE); Reinhold Deppisch, Hechingen (DE); Doris Deppisch, legal representative, Hechingen (DE); Silvia Koch, Albstadt (DE)

(73) Assignee: Gambro Lundia AB, Lund (SE)

( * ) Notice: Subject to any disclaimer, the term of this patent is extended or adjusted under 35 U.S.C. 154(b) by 240 days.

(21) Appl. No.: 12/680,531

(22) PCT Filed: Sep. 26, 2008

(86) PCT No.: PCT/EP2008/008195
§ 371 (c)(1),
(2), (4) Date: Sep. 3, 2010

(87) PCT Pub. No.: WO2009/040123
PCT Pub. Date: Apr. 2, 2009

(65) Prior Publication Data
US 2010/0320146 A1 Dec. 23, 2010

(30) Foreign Application Priority Data
Sep. 28, 2007 (EP) .................................... 07019105

(51) Int. Cl.
- *B01D 71/00* (2006.01)
- *B01D 69/00* (2006.01)
- *B01D 69/08* (2006.01)
- *B01D 67/00* (2006.01)

(52) U.S. Cl.
USPC ........... 210/490; 210/483; 210/488; 210/489; 210/500.21; 210/500.23; 210/500.24; 210/500.27; 264/48; 502/400; 502/402

(58) Field of Classification Search
USPC ..................... 210/483, 488, 489, 490, 500.23, 210/500.24, 500.27, 500.33, 500.41, 500.42, 210/638, 500.21; 502/400, 402; 264/48
See application file for complete search history.

(56) References Cited

U.S. PATENT DOCUMENTS

| | | | |
|---|---|---|---|
| 7,811,507 B2 * | 10/2010 | Wechs et al. .................. 264/562 |
| 8,136,675 B2 * | 3/2012 | Buck et al. ............... 210/500.23 |
| 2004/0026314 A1 * | 2/2004 | Kobayashi et al. ...... 210/500.24 |
| 2006/0144782 A1 * | 7/2006 | Buck ......................... 210/500.23 |
| 2006/0243657 A1 * | 11/2006 | Kobayashi et al. ...... 210/500.27 |
| 2007/0163949 A1 * | 7/2007 | Wechs et al. ............. 210/500.23 |
| 2008/0000828 A1 * | 1/2008 | Wechs et al. .................. 210/496 |
| 2010/0000942 A1 * | 1/2010 | Muller et al. ................. 210/636 |

* cited by examiner

Primary Examiner — John Kim
(74) Attorney, Agent, or Firm — Barnes & Thornburg LLP

(57) ABSTRACT

The invention relates to hydrophilic membranes which are supplemented or treated with a non-ionic surfactant and processes for preparing such membranes. The membranes are particularly suitable for plasma separation or for haemodialysis and haemodiafiltration, but can also advantageously be used in other applications. Accordingly, the invention is further directed to the use of such membranes for plasma separation, plasma filtration, micro filtration, plasma therapy, haemodialysis and haemodiafiltration or cell filtration applications, respectively. The treated hydrophilic membranes show excellent biocompatibility, such as reduced platelet drop and decreased TAT levels.

17 Claims, 9 Drawing Sheets

HYDROPHILIC MEMBRANES WITH A NON-IONIC SURFACTANT

CROSS REFERENCE TO RELATED APPLICATIONS

This application is a national phase application based on PCT/EP2008/008195 filed Sep. 26, 2008, which claims the benefit of European Application No. EP 07019105.1, filed Sep. 28, 2007, the contents of all of which are incorporated herein by reference.

BACKGROUND OF THE INVENTION

The invention relates to hydrophilic membranes which are supplemented or treated with a non-ionic surfactant and processes for preparing such membranes. The membranes are particularly suitable for plasma separation or for haemodialysis or haemodiafiltration, but can also advantageously be used in other applications. Accordingly, the invention is further directed to the use of such membranes for plasma separation, plasma filtration, micro filtration, plasma therapy, haemodialysis, haemodiafiltration or cell filtration applications, respectively. The coated hydrophilic membranes show excellent biocompatibility, such as reduced platelet drop and decreased TAT levels.

The invention particularly relates to the treatment of hydrophilic micro porous membranes which will preferably be used for plasma separation. Micro porous membranes have an average pore size of from about 0.05 µm to about 10.0 µm, but generally the selective pore size will not exceed 1 to 2 µm. Plasma separation or apheresis is a medical technology in which the blood of a donor or patient is separated into the plasma, i.e. the cell free component in blood, and the blood cells. Plasma separation may be conducted for several reasons. In the therapeutical plasmapheresis the separated plasma of a patient's blood is discarded and replaced by a substitute solution or by donor plasma, and is reinfused into the patient. This approach is useful in the treatment of several diseases and disorders. For example, in immunological diseases the plasmapheresis is useful to exchange antibodies, antigens, immune complexes or immune globulins. In non-immunological diseases the plasmapheresis allows for the depletion of metabolites, degradation products, as well as endogenous and exogenous toxins. In a variant of therapeutical plasmapheresis, plasma fractionation, the separated plasma of a patient's blood undergoes a second stage of further separation into high molecular and low molecular plasma fractions. The high molecular fraction is discarded, and the low molecular fraction of the plasma and the cellular components of the blood are reinfused into the patient. In another application, called plasma donation, the separated blood plasma from healthy donors is used for therapeutical plasma exchange or for the isolation of plasma components for pharmaceutical purposes.

The separation of whole blood into plasma and cellular components can be achieved either by centrifugation or by passing the blood through a plasma separation membrane. During the development of plasmapheresis, discontinuous centrifuges have been used first, which have then, at the beginning of the 70s, been replaced by continuous centrifugation systems. Centrifugation techniques have the advantage of being fast and cost effective; however, they often suffer from leaving impurities of cells or cell debris in the separated plasma. At the end of the 70s, the first membrane systems have been introduced for the plasmapheresis to overcome the disadvantages of centrifugation systems.

While being related to it, the requirements of plasma separation membranes are quite distinct from the requirements of dialysis membranes. Plasma separation uses the effect of separation by filtration, whereas dialysis rather uses osmosis and diffusion.

The sieving coefficient determines how much of a compound will be eliminated by a filtration process. The sieving coefficient is defined as the ratio of the concentration of a compound in the filtrate to the concentration of this compound in the blood. A sieving coefficient of "0" means, that the compound can not pass the membrane. A sieving coefficient of "1" means that 100% of the compound can pass the membrane. For the design of plasma separation membranes it is desirable that the whole spectrum of plasma proteins can pass the filtration membrane whereas the cellular components are completely retained.

The requirements of a plasma separation membrane for plasmapheresis can be summarized by the following characteristics: (1) high permeability or high sieving coefficient for the whole spectrum of plasma proteins and lipoproteins; (2) high surface porosity and total porosity of the membrane to achieve high filtration performance; (3) a hydrophilic, spontaneously wettable membrane structure; (4) low fouling properties for long term stable filtration; (5) low protein adsorption; (6) smooth surface in contact with blood; (7) low or no tendency to haemolysis during blood processing; (8) constant sieving properties and filtration behaviour over the whole treatment period; (9) high biocompatibility, no complement activation, low thrombogenicity; (10) mechanical stability; (11) sterilizability by steam, gamma radiation and/or ETO; (12) low amount of extractables.

Membranes which turned out to be especially suitable with regard to the above characteristics have been described in detail in European Patent Application No. 06116781.3 and European Patent Application No. 06116786.2, both of which are included herein by reference.

The material of the membranes according to the present invention is a polymer composition with relatively high hydrophilic properties. "Hydrophilic" membranes, in contrast to "hydrophobic" membranes can be defined, in accordance with the present invention, by their ability to be spontaneously water wettable without wetting aids. A membrane, independent of its shape, is called readily or spontaneously water wettable if it is wetted by water virtually spotlessly. When, for example, a piece of a flat membrane (50 mm in diameter) is stamped out of a dry test membrane and placed on water of 20° C. After one minute a visual check is made whether the membrane was spotlessly wetted by water. Hydrophilic membranes can alternatively be described as having a low contact angle with the applied water. Indeed, when a drop of water is placed on a hydrophilic, spontaneously wettable membrane or medium formed there from, the drop of liquid penetrates and wets the membrane, effectively providing a zero angle of contact therewith.

It is generally advantageous to use hydrophilic membranes in plasma separation applications, as such membranes show better performance with regard to filtration properties and have a reduced tendency to adsorb blood components and thus show a better blood compatibility. The above mentioned membranes belong to this group of advantageous, hydrophilic membranes.

Even though said membranes already show all of the characteristics which are needed for a membrane which is to be used for plasmapheresis, there are aspects which deserve improvement to achieve an even better performance. Such aspects are especially the improvement of thrombogenicity and a reduced interaction with blood components which can still be observed to a certain extend with hydrophilic membranes.

The invention is also directed to semipermeable hydrophilic membranes for haemodialysis or haemodiafiltration which are treated or supplemented with a non-ionic surfactant for improving the biocompatibility of such membranes, especially their thrombogenicity.

The expression "non-ionic surfactants" as used herein refers to a surfactant which does not dissociate is called a non-ionic surfactant. The molecules are uncharged. The hydrophilic group of non-ionic surfactants is a polymerized alkylene oxide, preferably ethylene oxide (a water soluble polyether with 10 to 100 units length typically). Non-ionic surfactants include alcohol ethoxylates, alkylphenol ethoxylates, phenol ethoxylates, amide ethoxylates, glyceride ethoxylates (soya bean oil and castor oil ethoxylates), fatty acid ethoxylates, and fatty amine ethoxylates. Other significant non-ionic surfactants are the alkyl glycosides in which the hydrophilic groups are sugars (polysaccharides). Preferred non-ionic surfactants in the context of the present invention are polyoxyethylene sorbitan surfactants.

The invention is also directed to a method of treating semipermeable hydrophilic membranes for haemodialysis or haemodiafiltration with a non-ionic surfactant, preferably polyoxyethylene sorbitan surfactants, more preferably with polyoxyethylene sorbitan monolaurate (polysorbate 20 or Tween® 20).

Attempts to improve the performance of hydrophobic membranes are well known in the prior art, as such membranes generally suffer from low filtration property and a high tendency to adsorb blood components.

In EP 0 188 104 A2 methods are described for improving the wettability of a porous, hydrophobic polymer surface, e.g. made from polypropylene, polyester, polyethylene and/or polyurethane, by spraying or dipping the polymer surface into a preferably non-aqueous solution of e.g. polysorbate 20, 40, 60 or 80, directly followed by drying. The concentration of polysorbate in the solution used lies in the range of about 0.1-0.5% w/v.

In JP 61-133105, methods are described for improving the permeability and wettability of a hydrophobic porous membrane, preferably made of polyethylene, by immersing the membrane in an aqueous solution containing 0.001-10% (w/w) of e.g. polyoxyethylene sorbitan fatty acid ester for a certain time, followed by drying.

In JP 63-277251 discloses methods for improving water permeability of porous, hydrophobic polysulfone-based membranes having a pore-size of 0.01-5 μm by immersing the membrane in e.g. an aqueous solution containing 0.001-15% w/w of e.g. a polyoxyethylene sorbitane alkyl ester surfactant (monolaurate) for a certain time, followed by high-frequency drying.

EP 1 334 763 B1 also claims porous, hydrophobic polysulfone-based membranes which are coated on the surface with 0.002-25% w/w of a polyoxyethylene sorbitane surfactant, such as have been described already in JP 63-277251. The only difference to JP 63-277251 lies in the method of applying the surfactant as it additionally includes a step of rinsing the membrane to remove excess surfactant from the membrane.

However, none of the above-mentioned references, nor any other prior art mentions that not only hydrophobic membranes can be improved by an additional treatment with a non-ionic surfactant, but that, surprisingly, also hydrophilic membranes can be improved by such treatment. This is astonishing since one would assume that hydrophilic membranes do not require an improvement of wettability or water permeability like it is obviously the case with hydrophobic membranes. In fact, it is already surprising that hydrophilic membranes can be coated with a polyoxyethylene sorbitan at all to an extent that makes a difference to the biocompatibility of such hydrophilic membrane.

SUMMARY OF THE PRESENT INVENTION

The present invention is based on the finding that, surprisingly, a hydrophilic membrane can be treated with a non-ionic surfactant, and that such coating makes a difference with regard to blood compatibility of the treated membrane.

The object of the present invention therefore was to provide a hydrophilic membrane, preferably a hollow fiber membrane, for medical use, particularly for use in plasma separation applications, as well as a hollow fiber membrane used for haemodialysis or conventional haemodiafiltration, having improved properties over the prior art membranes, especially in respect of high blood compatibility and decreased interaction with blood components, and a process of preparing such membrane.

This and other objects are solved by a membrane being obtainable or obtained by the process of the present invention. Thus, according to the present invention there is also provided a process for preparing an improved hydrophilic membrane.

DETAILED DESCRIPTION OF THE INVENTION

Figure 1:
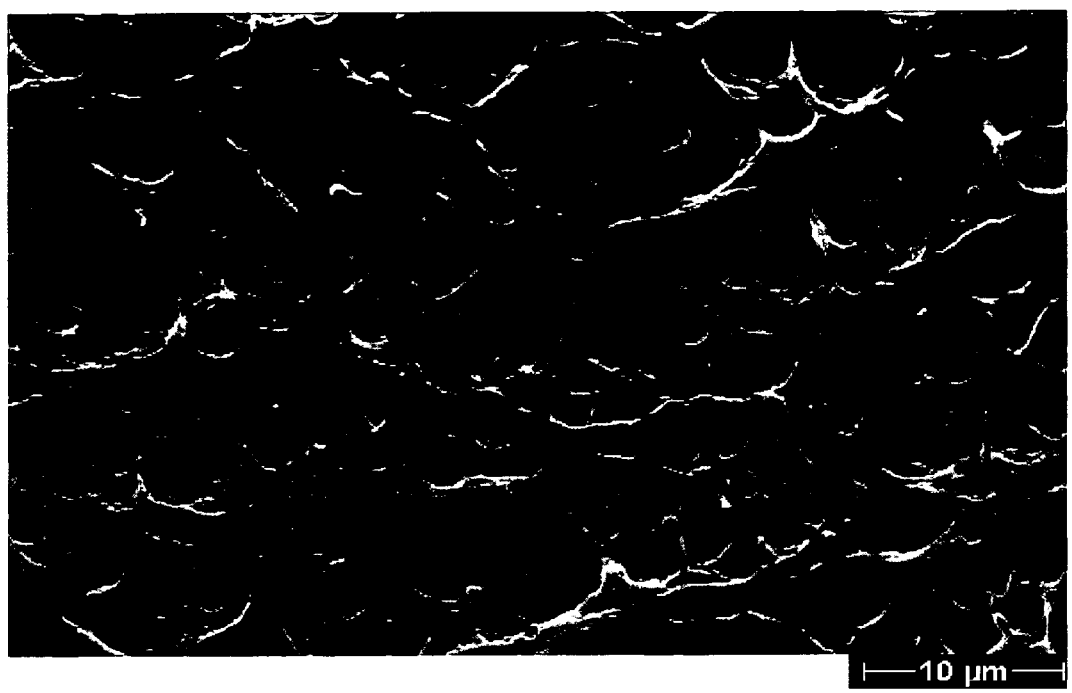
FIG. 1: Scanning Electron Micrograph (SEM) showing the morphology of the blood contacting surface (inner side) of a plasma separation membrane which can be treated according to invention.

The membranes which are treated according to the present invention are, for example, porous, hydrophilic membranes, preferably hollow fiber membranes, which are preferably used for plasmafiltration. Other membranes which can be treated according to the invention encompass hydrophilic semipermeable membranes, which are preferably used for haemodialysis or haemodiafiltration. The membranes described herein may be prepared using any suitable polymers which will result in a hydrophilic membrane, preferably a hollow fiber membrane, which meets the required biocompatibility requirements and properties. Such membrane materials and surfaces must be highly biocompatible and resist clotting, protein adhesion and detrimental interaction with immune system components. The structural strength of the hollow fiber membranes must be high enough to safely withstand hydraulic and physical perturbations.

The membranes used for plasmafiltration also must be designed with a morphology capable of separating plasma from whole blood by filtering from the inside (lumen) of the fiber to the outside.

A number of potentially suitable polymer fiber membrane materials which can be used for the preparation of the above-mentioned membranes include polyurethane, polypropylene, polysulfone, polyethersulfone, polycarbonate, nylon, polyimide, silicone, or other synthetic resins or combinations of two or more polymers known to those skilled in the art. A preferred polymer is polysulfone, and more preferably polyethersulfone and polyarylethersulfone. Such polysulfone fibers can be produced in the presence of polymer dopes, core fluids, and coagulation fluids using processes including membrane spinning methods which achieve the desired product. Examples of such additive materials used in the polymerization process, spinning process and/or fiber membrane production include polyvinyl pyrrolidone, N-alkyl-2-pyrrolidone, N-methyl-2-pyrrolidone, dimethyl acetomide, dimethyl sulfoxide, and mixtures of two or more such materials.

Preferably, membranes which are treated according to the present invention are hydrophilic micro porous membranes, preferably hollow fiber membranes, comprising at least one of polysulfone, polyethersulfone or polyarylethersulfone and further comprising polyvinylpyrrolidone (PVP) and N-alkyl-2-pyrrolidone (NAP) or N-methyl-2-pyrrolidone (NMP).

More preferably, membranes which are treated according to the present invention are micro porous, hydrophilic membranes, preferably having hollow fiber geometry. The process for preparing a preferred membrane according to the invention comprises the steps of
  i. extruding a polymer solution through the outer ring slit of a hollow fibre spinning nozzle, simultaneously extruding a centre fluid through the inner bore of the hollow fibre spinning nozzle, into a precipitation bath, whereby
  ii. the polymer solution contains 10 to 26 wt-% of polysulfone (PSU), polyethersulfone (PES) or polyarylethersulfone (PAES), 8 to 15 wt-% polyvinylpyrrolidone (PVP), 55 to 75 wt-% N-alkyl-2-pyrrolidone (NAP) or N-methyl-2-pyrrolidone (NMP) and 3 to 9 wt-% water,
  iii. the centre fluid contains 70 to 90 wt-% N-alkyl-2-pyrrolidone (NAP) or N-methyl-2-pyrrolidone (NMP) and 10 to 30 wt-% water, and
  iv. the precipitation bath contains 0 to 20 wt-% N-alkyl-2-pyrrolidone (NAP) or N-methyl-2-pyrrolidone (NMP) and 80 to 100 wt-% water.

In one embodiment of said process the polymer solution contains 15 to 21 wt-% of polysulfone (PSU), polyethersulfone (PES) or polyarylethersulfone (PAES), 10 to 12,5 wt-% polyvinylpyrrolidone (PVP) and 60 to 70 wt-% N-alkyl-2-pyrrolidone (NAP).

In another embodiment of said process the polymer solution contains 17 to 19 wt-% of polysulfone (PSU), polyethersulfone (PES) or polyarylethersulfone (PAES), 10,75 to 11,75 wt-% polyvinylpyrrolidone (PVP) and 63 to 66,5 wt-% N-alkyl-2-pyrrolidone (NAP).

In another embodiment of said process the polymer solution contains 4 to 8 wt-% water. In yet another embodiment of the process of the present invention the polymer solution contains 5 to 7 wt-% water. In yet another embodiment of the process of the present invention the polymer solution contains about 6 wt-% water.

In such embodiments of the process it is required that the centre fluid contains 70 to 90 wt-% N-alkyl-2-pyrrolidone (NAP) and 10 to 30 wt-% water.

In such embodiments of the process it is further required that the precipitation bath contains 0 to 20 wt-% N-alkyl-2-pyrrolidone (NAP) and 80 to 100 wt-% water. Using in the precipitation bath more that 20 wt-% N-alkyl-2-pyrrolidone (NAP) causes the membrane to become instable during membrane formation.

Methods for preparing such micro porous membranes are generally known to persons with skill in the art or described in detail in the above-mentioned European Patent Applications Nos. 06116781.3 and 06116786.2.

FIG. 1 depicts a scanning electron micrograph (SEM) showing the morphology of the blood contacting surface of a plasma separation membrane which can be treated according to the invention.

Preferably, plasmafiltration membranes which are treated according to the present invention are characterized by a total plasma protein sieving coefficient of >0.90, preferably >0.95. For plasma separation applications it is preferred that the hollow fibre membrane shall have an inner diameter in the range of 100 to 500 μm, preferably 150 to 450 μm, more preferably 200 to 400 μm. Lower inner diameters are disadvantageous because they result in too high wall shear rates and increased pressure drop in the fibre or in the whole filtration module. On the other hand, if the inner diameters are too high, this would result in too low shear rates which increase the risk of haemolysis at low transmembrane pressures (TMP). It is further preferred for plasma separation applications that the hollow fibre membrane shall have a wall thickness in the range of 20 to 150 μm, preferably 30 to 125 μm, more preferably 40 to 100 μm. Lower wall thicknesses are disadvantageous due to reduced mechanical properties of the fibre during production and during its use in the plasma separation module itself. Higher wall thicknesses are disadvantageous because they require increased time intervals to perform the phase inversion process resulting in instable process conditions and an instable membrane. It is further preferred for plasma separation applications that the hollow fibre membrane shall have an average pore diameter of the selective separation layer in the membrane in the range of 0.1 to 1 μm, preferably 0.1 to 0.7 µm, more preferably 0.1 to 0.4 µm. Lower average pore diameters of the selective separation layer are disadvantageous due to incomplete passage of total plasma proteins through the porous structure. Higher average pore diameters of the selective separation layer are disadvantageous due to an increased risk of haemolysis (cell rupture).

Other membranes which can be treated according to the present invention are hydrophilic semipermeable membranes, preferably hollow fiber membranes, which are used for haemodialysis or haemodiafiltration.

Such membranes which are treated according to the present invention preferably are hollow fiber membranes, comprising at least one of polysulfone, polyethersulfone or polyarylethersulfone and further comprise polyvinylpyrrolidone (PVP) and N-methyl-2-pyrrolidone (NMP). They may further comprise other hydrophobic polymers, preferably in a low amount of 0.01 to 5 wt.-% of the total weight of the polymer solution used for preparing the membrane, such as, for example, polyamide.

Preferably, said hydrophilic semipermeable membranes are asymmetric membranes having an average pore size of from about 1 nm to about 20 nm. Preferably, the average pore size is below 8 nm, more preferably below 6 nm. Such membrane is further characterized by a sieving coefficient for albumin of below 0.01.

Preferably, such membrane comprises polysulfone, polyethersulfone or polyarylethersulfone in an amount of 10 to 30 wt.-% of the total weight of the polymer solution used for preparing the membrane. Preferably, the amount is 10 to 20 wt.-%. Polyethersulfone and polyarylethersulfone are preferred, polyarylethersulfone is especially preferred.

The hydrophilic component of the polymer solution, PVP, preferably consists of 50-90 wt.-% (by weight of the total weight of the hydrophilic polymer) of a low molecular weight component having a molecular weight of less than 100 000, and 10-50 wt.-% of a high molecular weight component having a molecular weight of 100 000 or more. The ratio of the low molecular weight component to the high molecular weight component can also be defined as being between 1:7 and 7:1.

The preferred content range by weight of the total weight of the solution for preparing a hydrophilic semipermeable membrane is 10-30 wt.-%, preferably 10-20 wt.-% for polysulfone, polyethersulfone or polyarylethersulfone, and 2-20 wt.-%, preferably 3-15 wt.-% for PVP.

For the preparation of a preferred hydrophilic haemodialysis membranes used in Example 6, it is required that the centre fluid contains 40 to 50 wt-% N-methyl-2-pyrrolidone (NMP) and 50 to 60 wt-% water, preferably 43 to 48 wt-% N-methyl-2-pyrrolidone (NAP) and 53 to 59 wt-% water. The spinning solution comprises 10 to 20 wt.-% of polyarylethersulfone and 5 to 9 wt.-% polyvinylpyrrolidone, wherein the polyvinylpyrrolidone consists of a low molecular weight component and a high molecular weight component as described before.

Methods for preparing such hydrophilic semipermeable membranes are generally know and are described, for example, in U.S. Pat. Nos. 4,935,141 A, 5,891,338 A, 6,355,730 B1 or EP 1 715 941 A1.

The shape of the hydrophilic membranes treated and used according to the present invention is not particularly limited and may be tubular, flat or, preferably, hollow fiber shape.

The above-described hydrophilic membranes can be treated with a solution of a non-ionic surfactant as described before. Preferably, such non-ionic surfactant is an aqueous solution of at least one polyoxyethylene sorbitan surfactant. Preferably, said polyoxyethylene sorbitan is selected from the group consisting of polyoxyethylene sorbitan acyl ester, polyoxyethylene sorbitan monolaurate, polyoxyethylene sorbitan monopalmitate, polyoxyethylene sorbitan monostearate, polyoxyethylene sorbitantristearate and polyoxyethylene sorbitanmonooleate, such as, for example, Polysorbate 20 (Tween® 20 or Polyoxyethylene (20) sorbitan monolaurate), Polysorbate 40 (Tween® 40 or Polyoxyethylene (20) sorbitan monopalmitate), Polysorbate 60
(Tween® 60 or Polyoxyethylene (20) sorbitan monostearate) and Polysorbate 80 (Tween® 80 or Polyoxyethylene (20) sorbitan monooleate). Each of the polyoxyethylene sorbitan compounds mentioned can be used either alone or in combination with another polyoxyethylene sorbitan.

In the context of the present invention, polyoxyethylene sorbitan monolaurate is preferred. Polysorbate 20, commercially known as Tween® 20 (CAS No. 9005-64-5), is especially preferred for treating a membrane according to the invention in order to improve biocompatibility, such as reduced platelet drop and decreased TAT levels. Polysorbate 20 is a polysorbate surfactant whose stability and relative non-toxicity allows it to be used as a detergent and emulsifier in a number of domestic, scientific, and pharmacological applications. It is a polyoxyethylene derivative of sorbitan monolaurate, and is distinguished from the other members in the Tween range by the length of the polyoxyethylene chain. The commercial product contains a range of chemical species.

Membranes can be treated according to the invention with solutions consisting essentially of an aqueous solution of at least one of the above-mentioned polyoxyethylene sorbitan compounds or combinations thereof. Preferably, the solution contains from 0.05 wt.-% to 20 wt.-% of such polyoxyethylene sorbitan. The concentration of polyoxyethylene sorbitan preferably is from 0.1 wt.-% to 10 wt.-%, more preferably from 0.2 wt-% to 5 wt.-% and even more preferably from 0.2 to 2 wt.-%. A concentration of from 0.2 to 1.5 wt.-% polyoxyethylene sorbitan has proved to be especially advantageous.

Accordingly, it is preferable to treat a membrane according to the invention with a solution having from 0.05 wt.-% to 20 wt.-% Polysorbate 20 dissolved in water, more preferably having from 0.1 wt.-% to 10 wt.-%, more preferably from 0.2 wt-% to 5 wt.-% and even more preferably from 0.2 to 2 wt.-% Polysorbate 20 dissolved in water and most preferably having from 0.2 wt.-% to 1.5 wt.-% Polysorbate 20 dissolved in water.

The water used for preparing the polyoxyethylene sorbitan solution is preferably demineralised and degassed.

The membrane is preferably treated within a housing having an inlet and outlet part, i.e. the treatment is performed with, for example, a filter device comprising the membrane. While it is also possible to treat any membrane according to the invention outside of a housing, the coating process is improved by having the membrane or membrane fibers distributed homogenously within the housing, thus enabling a homogenous distribution of the polyoxyethylene sorbitan solution and, accordingly, a more homogenous coating of the membrane. The efficiency of the coating process is also improved as, for example, the filter may subsequently be processed further into the final product without having to handle the treated membrane again. However, it is also possible to treat the membrane before it has been transferred into such housing, depending e.g. on its final purpose. In case the treatment is done before transferring the membrane to a housing, treatment can be done by dipping or immersing the membrane in the solution, by spraying the solution onto the membrane or by rinsing the membrane with the solution.

It is also possible to introduce the polyoxyethylene sorbitan during the spinning process as a component of the polymer and/or the centre solution. For example, it is possible to modify the polymer recipe and add polyoxyethylene sorbitan into the polymer solution reducing the solvent content of an existing polymer recipe. The amount added can be varied between 0.1 and 10 wt.-%, preferably between 0.1 and 5 wt.-%. The spinning conditions have to be adjusted to achieve a microporous sponge like structure that has the required separation characteristics and surface properties. It is also possible to reduce the amount of polyoxyethylene sorbitan used in the manufacturing process of the membrane by adding the component to the center (bore) liquid. The amount of polyoxyethylene sorbitan in the center (bore) liquid has to be adjusted to the spinning conditions and can be varied between 0.1 and 10 wt.-%, preferably between 0.1 and 5 wt.-%. Also triple spinnerets (or multi layer spinnerets) can be used to manufacture this type of membrane. In this case only one polymer solution of the two used in the triple spinneret (forming two polymer layers on top of each other, forming the wall of the membrane) contains polyoxyethylene sorbitan. It is preferred to add polyoxyethylene sorbitan to the solution forming the blood contacting surface.

The present invention is, therefore, also directed to a method and process for treating a hydrophilic membrane, preferably a hydrophilic hollow fiber membrane, and especially preferably a hydrophilic, microporous hollow fiber membrane.

The process for treating a membrane after its preparation and according to the invention with a polyoxyethylene sorbitan solution can be summarized as follows:
  (a) providing a polyoxyethylene sorbitan solution in water;
  (b) contacting the hydrophilic membrane with the solution;
  (c) removing the solution from the membrane, wherein the amount of solution remaining on the membrane should not exceed 25%, preferably 15% of the total amount of solution applied to the membrane in step (b);
  (d) drying the membrane.

Accordingly, in a first step, the solution is prepared by dissolving the polyoxyethylene sorbitan in water. Demineralised and degassed water is preferred. Polyoxyethylene sorbitan compounds such as Polysorbate 20 tend to be highly viscous. Therefore, the solution should be carefully stirred after the polyoxyethylene sorbitan has been added to the water, preferably at room temperature, for about 5 to 30 minutes. In general, 15 minutes are sufficient.

In a second step, the filter or any suitable container having distributed therein the membrane to be treated/coated are filled with the polyoxyethylene sorbitan solution. If a filter device is used, the air should be removed from the blood and filtrate side in the course of the filling operation. The amount of solution used can be adapted to the filter type or container used. The solution may remain in the filter with closed ports for a given time without shaking or otherwise moving the filter and/or the solution inside before the solution is again removed from the device. However, it is advantageous to circulate the solution through the filter device, e.g. by establishing a flow of the polyoxyethylene sorbitan solution from the inlet to the outlet of the housing by means known to a person skilled in the art. Ciiculating the solution improves the homogenous distribution of the polyoxyethylene sorbitan within the filter and, as a consequence, its homogenous adsorption to the membrane. Further, the time and/or amount of polyoxyethylene sorbitan which is needed for obtaining a sufficient and homogenous coating of the membrane can be reduced.

The membrane may be contacted with the polyoxyethylene sorbitan solution for some minutes up to several hours. Preferably, the treatment will take from 1 minute to about 2 hours. In case the membrane is contacted with the polyoxyethylene sorbitan less than 1 or 2 minutes the amount of polyoxyethylene sorbitan on the membrane will be insufficient. Treatment times above 2 or 3 hours, while possible, are not efficient as the effect of the polyoxyethylene sorbitan adsorbed to the membrane in terms of biocompatibility will not improve any more after a certain time. Preferably, the treatment time is from between 2 to 60 minutes, more preferably from 5 to 45 minutes. A treatment time of about 10 to 30 minutes proved to be efficient. In order to improve the time efficiency of the treatment, the concentration of the polyoxyethylene sorbitan in the solution can be increased while the treatment time is decreased from, for example, 30 minutes with a 1 wt.-% Polysorbate 20 solution to 10 minutes with a 2 wt.-% solution of Polysorbate 20.

The temperature during such exposure of a membrane to a polyoxyethylene sorbitan solution may vary over a broad range. Temperatures from between 4° C. to about 60° C. may, for example, be efficiently used for the described process. Preferred temperatures for treating a membrane with a polyoxyethylene sorbitan solution according to the invention will range from between 4° C. to 40° C. Good results have been obtained by performing the treatment at room temperature, i.e.

from between 18° C. to 25° C., which is a preferred temperature range also with regard to the efficiency of the process.

Figure 2:
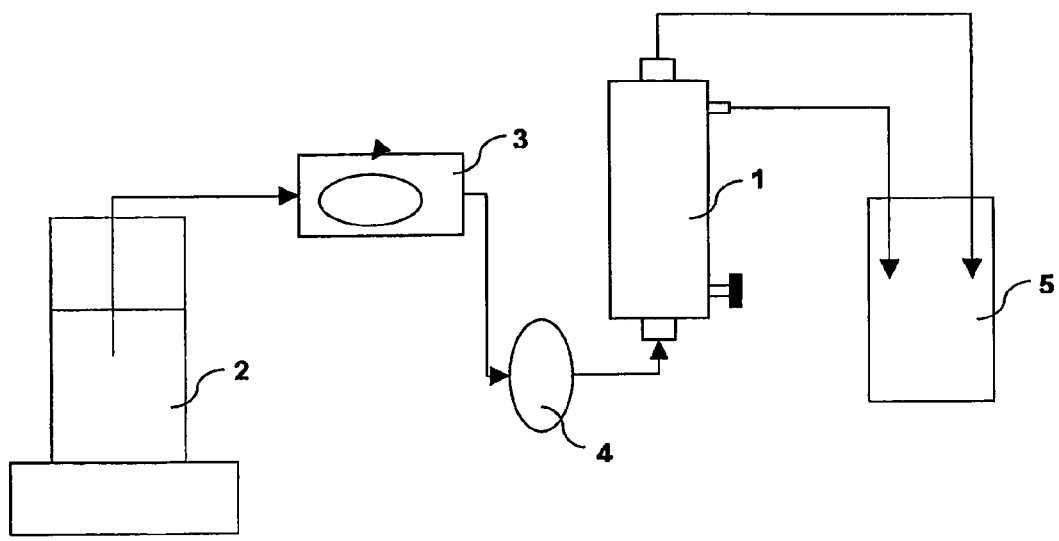
FIG. 2: Schematic set-up for a possible way of treating a membrane with a non-ionic surfactant within a housing (1). The set-up depicts a stationary treatment of the membrane. The solution of the surfactant (2) is transferred to the housing with the help of a pump (3), whereby it passes a sterile filter (4). After a given time wherein the solution remains in the filter, the used solution is collected in another vessel (5).

As an optional step and depending on the specific membrane to be treated, it may be advisable to repeat such treatment cycle at least once. It is especially advisable to repeat subjecting the membrane to the solution at least twice in cases where the polyoxyethylene sorbitan solution is not circulated through the filter or container but is stationary. In this case the solution is removed from the filter or container comprising the membrane and the filter or container is again filled as described before. It is possible to reuse the polyoxyethylene sorbitan solution for an additional treatment cycle, even though a fresh polyoxyethylene sorbitan solution may be used as well. For example, the membrane may be subjected to a 1 wt.-% polyoxyethylene sorbitan solution twice for e.g. 30 minutes. FIG. 2 depicts a possible set-up for the treatment of a membrane within a housing.

In a third step, the polyoxyethylene sorbitan solution is thoroughly removed from the filter or container, whereby care should be taken to remove as much of the solution as possible. Preferably, not more than 25 wt.-%, more preferably 15 wt.-% of the initial solution submitted to the membrane should remain on the membrane and/or within the filter device, respectively. Even more preferably, the amount of solution remaining on the membrane and/or within the filter device should not exceed 12%, especially preferably not exceed 8% of the initially used solution.

Optionally, the membrane can be rinsed in a subsequent step with a solvent wherein the respective non-ionic surfactant is soluble. However, such rinsing step proved to be not mandatory to arrive at membranes with a homogenous coating and a significantly improved performance with regard to biocompatibility. In case of rinsing, possible solvents are, for example, water, aqueous solutions of electrolytes such as saline buffer solutions, for example, phosphate buffer solution, alcohols, such as ethanol or methanol or mixtures thereof, organic solvents, such as pyridine, chloroform, cyclohexane, ethyl acetate, toluene or mixtures thereof. Water and aqueous solutions of electrolytes are preferred for polyoxyethylene sorbitan surfactants. In this case, water is especially preferred for an optional rinsing step.

In a fourth step, the membrane is dried. Drying is preferably done by subjecting the coated membrane to an air stream, preferably at elevated temperatures from between 30° C. to 60° C. In the case of a filter device, flow rates may vary over a relatively wide range. Flow rates from between 1 and 10 Nm$^3$/h may be used without adverse effects to the membrane and its properties. Advantageously, the air is passed through the filter/membrane with pressure so as to also remove residual polyoxyethylene sorbitan from the membrane, especially in cases where no rinsing step was performed. The pressure used can be adapted to the membrane used to avoid damaging the membrane. The time needed for drying depends upon the temperature and flow rates used, as well as on the amount of polyoxyethylene sorbitan solution which remains on the membrane and/or housing. In general, drying should be continued until the amount of residual water is below 10 g per 0.5 m$^2$ of the membrane material, preferably below 5 g per 0.5 m$^2$. Most preferably it is between 0 g and 1 g per 0.5 m$^2$.

A membrane which has been prepared/treated according to the invention can be directly packed and, for example, steam-sterilized without adverse effects to the membrane comprising a non-ionic surfactant according to the invention. It is also possible to submit the treated membrane to ETO sterilization or dry gamma-ray sterilization. It is, however, preferred to use steam-sterilization. It is also possible to treat a membrane according to the invention after it has been steam-sterilized. Such membrane will have to be sterilized again after the treatment, either by a second steam-sterilization or, alternatively, by ETO sterilization.

The amount of polyoxyethylene sorbitan finally adsorbed to a membrane can be determined indirectly, for example, by measuring the amount of polyoxyethylene sorbitan in the pooled fractions of the polyoxyethylene sorbitan solution which are removed from the treatment vessel, e.g. the filter, in the above-described steps. The amount of polyoxyethylene sorbitan in said pooled fractions can be determined quantitatively by Reversed Phase HPLC (Example 3) and compared to the amount of polyoxyethylene sorbitan initially applied to the membrane.

The amount adsorbed to a hydrophilic membrane according to the present invention is from between 1 mg and 200 mg per unit dry weight (g) of the hydrophilic membrane. Preferably, the amount is from between 50 mg and 100 mg per unit dry weight (g) of the hydrophilic membrane (Example 4).

In order to assess the amount of polyoxyethylene sorbitan which is eventually released into a patient during a treatment involving, for example, a plasma filtration membrane which was coated according to the invention, tests were performed based on a simulated plasmapheresis treatment (Example 5). In such tests it could be shown that the polyoxyethylene sorbitan released during a standard treatment is very low. The total amount released is, for example, far below the ADI which has been established by the FAO/WHO Expert Committee on Food Additives.

Polysorbates are also approved by the FDA as inactive ingredients in drug products. For intravenous infusion and injection the maximum allowed concentration for Polysorbate 20 ranges from 0.4% to 2.5%.

The following three methods were used to characterize the biocompatibility properties of the coated hydrophilic membranes. It should be noted that the single values observed in a given experiment cannot necessarily be compared with the single values of another experiment of the same kind, as the absolute values achieved in an experiment will be strongly dependent upon the specific donor blood. Therefore, positive and negative controls are done within one experiment to allow interpreting the results.

Thrombin-Antithrombin III (TAT) levels are measured and platelet counts are done after passage of platelet rich plasma (PRP) along the membrane and in the pool as a marker for thrombogenicity. The experiment is carried out in a recirculation modus as a high volume of plasma is required to test in the "single pass modus" (Example 6).

Figure 3:
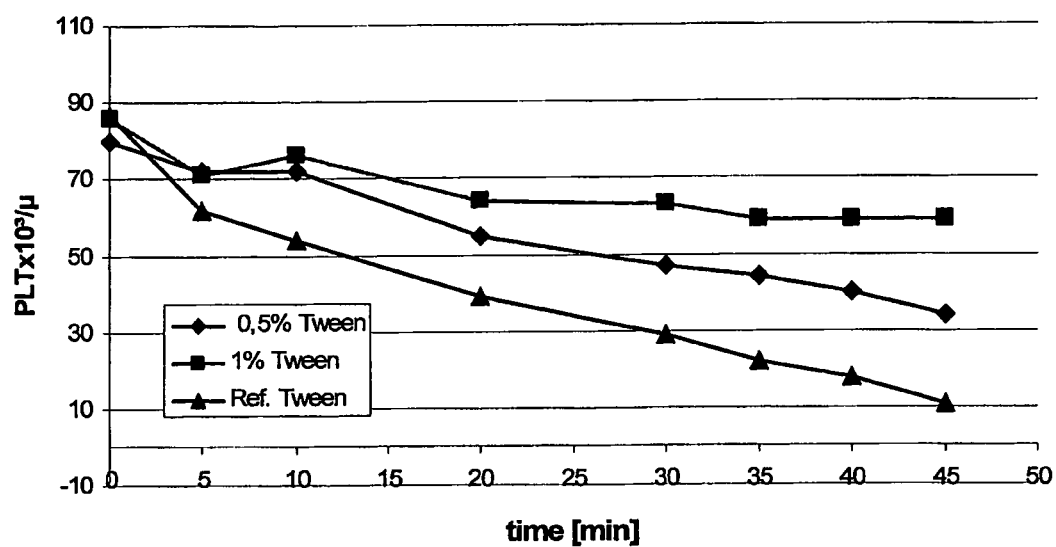
FIG. 3: Platelet count (blood out, UF corrected) of an untreated micro-porous membrane (-▲-) and a micro porous membrane treated with a 1.0 wt.-% (-■-) and a 0.5 wt.-% (-♦-) solution of Polysorbate 20.
Figure 4:
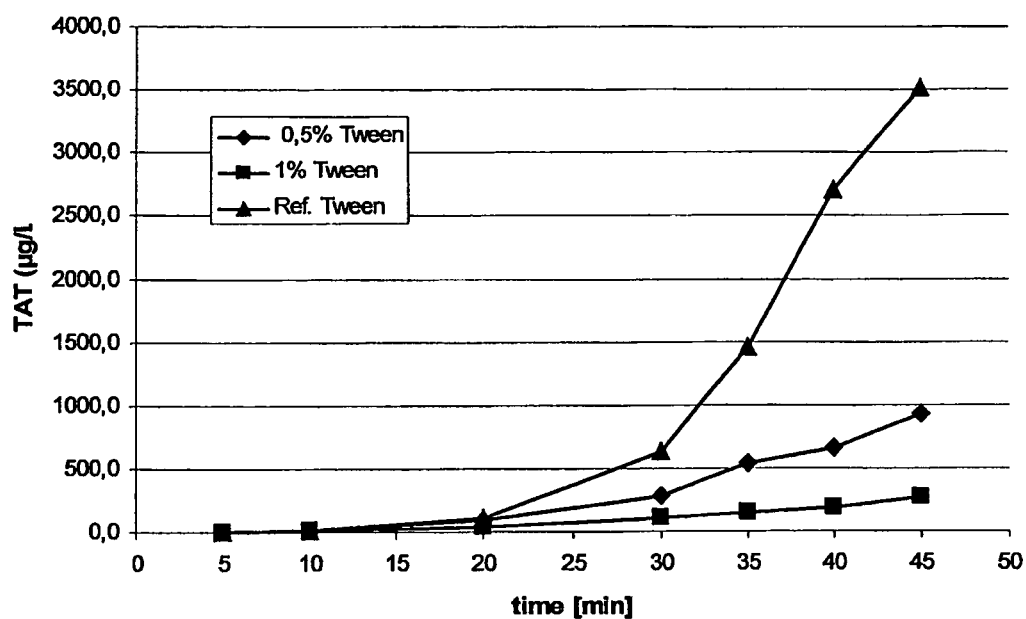
FIG. 4: TAT generation (blood out) of an untreated micro-porous membrane (-▲-) and a micro porous membrane treated with a 1.0 wt.-% (-■-) and a 0.5 wt.-% (-♦-) solution of Polysorbate 20.
Figure 8:
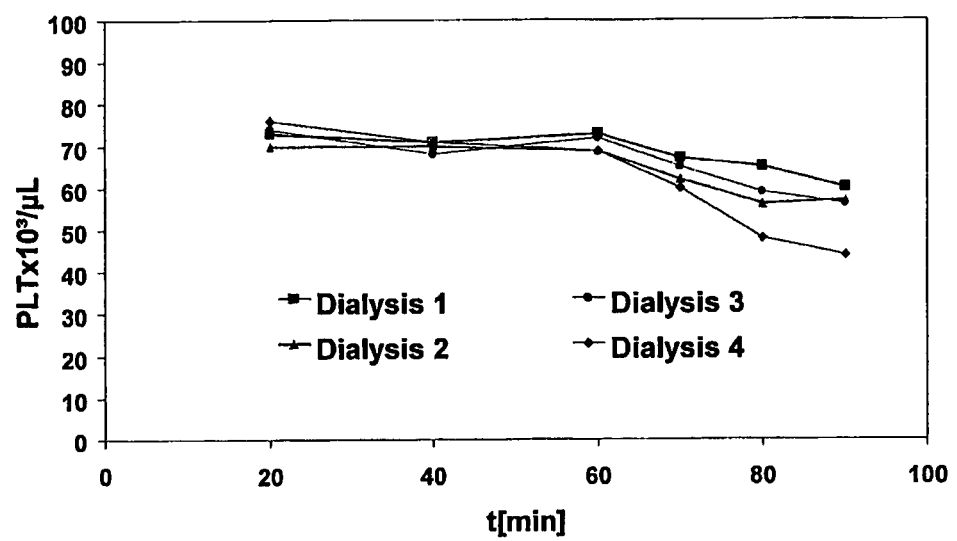
FIG. 8: Platelet counts during perfusion of a hydrophilic semipermeable dialysis hollow fiber membrane. The membranes depicted as Dialysis 1 (-■-) and Dialysis 2 (-▲-) were pre-treated with Polysorbate 20 (0.2 wt.-%). The membrane depicted as Dialysis 3 (-●-) corresponds to membrane Dialysis 1 and 2 but has not been treated with Polysorbate 20. The membrane depicted as Dialysis 4 (-♦-) is another untreated membrane with a slightly different recipe.
Figure 9:
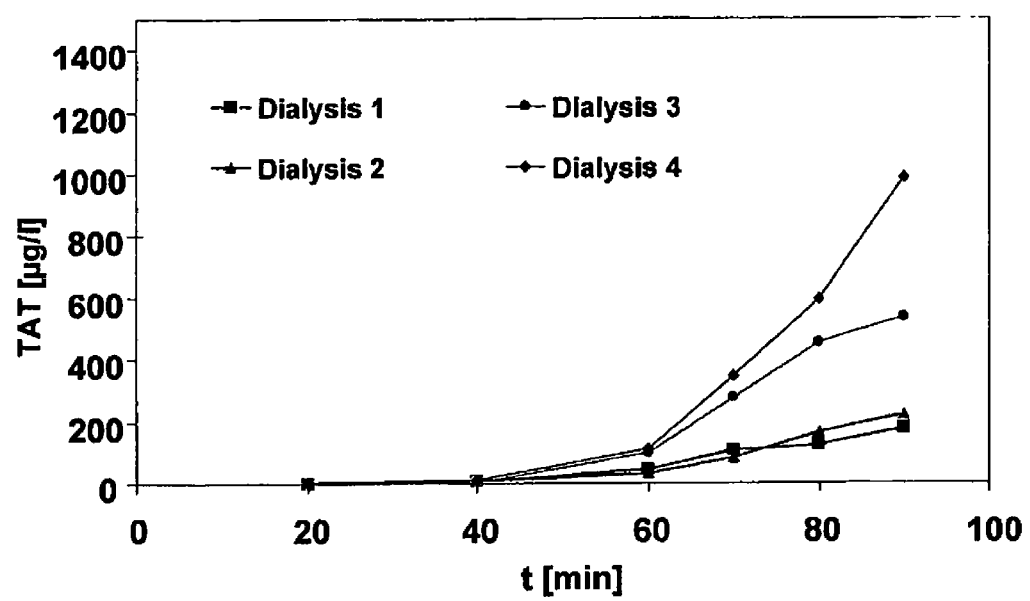
FIG. 9: TAT generation of hydrophilic semipermeable dialysis hollow fiber membranes. The membranes depicted as Dialysis 1 (-■-) and Dialysis 2 (-▲-) were pre-treated with Polysorbate 20 (0.2 wt.-%). The membrane depicted as Dialysis 3 (-●-) corresponds to membrane Dialysis 1 and 2 but has not been treated with Polysorbate 20. The membrane depicted as Dialysis 4 (-♦-) is another untreated membrane with a slightly different recipe.

During the thrombogenicity evaluation of the untreated micro porous membrane plasmafilter minimodule, a larger platelet drop and a larger TAT generation was observed in comparison to the same micro porous membrane which had been treated with Polysorbate 20 (FIGS. 3 and 4)). In case of a hydrophilic haemodialysis membrane which was subjected to a treatment according to the invention, TAT generation and platelet drop show that the treated membrane has an improved thrombogenicity compared to the non-treated version (FIGS. 8 and 9).

Complement activation, as generated by the terminal complement complex (TCC), is measured before and after the passage of fresh human plasma through the minimodule. Additionally, the generation of TCC in the filtrate is measured. The experiment is carried out in a single pass modus. The details of the complement activation measurement are as described by Deppisch, R., et al., *Fluid Phase Generation of Terminal Complement Complex as a Novel Index of Biocompatibility*. Kidney International, 1990. 37: p. 696-706. Complement activation is not only related to cellular activation but also to the activation of the plasmatic fraction. In the case of plasma separation and subsequent treatment, for example adsorption, double filtration complement activation becomes a major issue. In case of increased complement activation, i.e. generation of TCC, the activated plasma may cause severe health problems to a patient, if it is re-infused into a patient.

Figure 5:
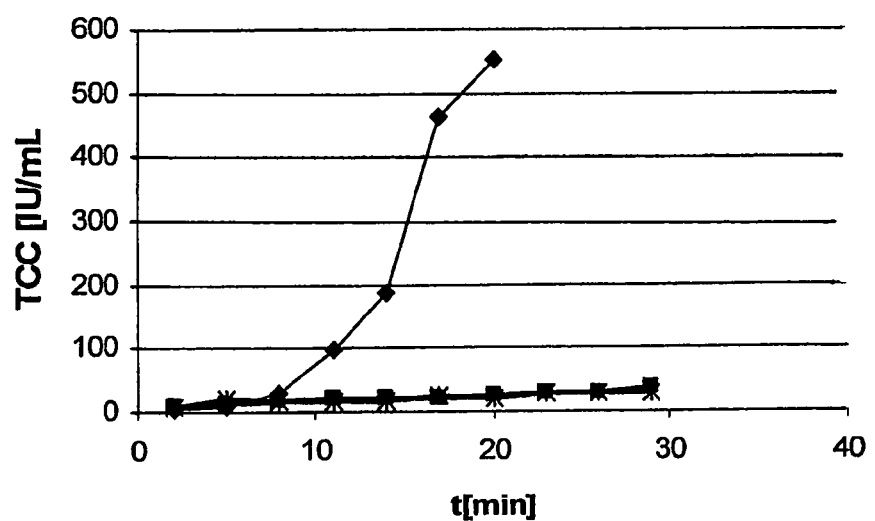
FIG. 5: TCC generation (blood out) in plasma during perfusion of an untreated micro-porous membrane (-★-) and a micro porous membrane treated with a 1.0 wt.-% (-■-) Polysorbate 20. TCC generation of a Cuprophan® membrane (-♦-) is shown for comparison.
Figure 6:
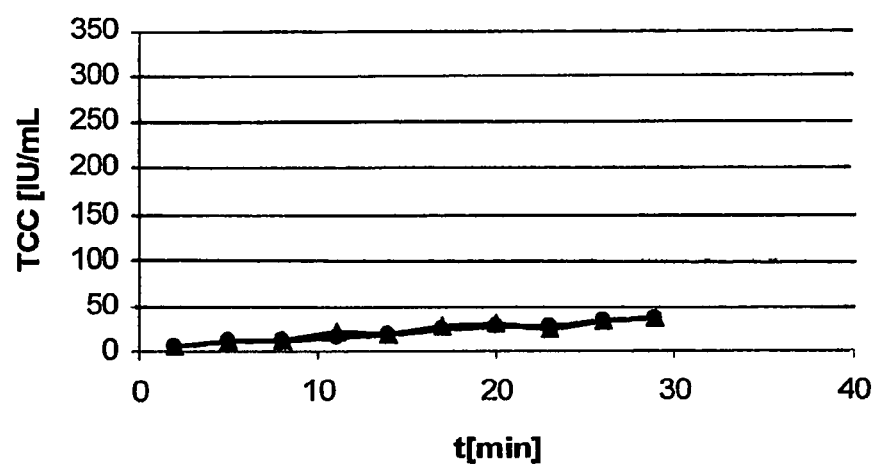
FIG. 6: TCC generation (UF) during perfusion of an untreated micro-porous membrane (-●-) and a micro porous membrane treated with a 1.0 wt.-% (-▲-) Polysorbate 20.

The generation of the terminal complement complex was assessed during perfusion of miniaturized devices with human plasma (Example 7). The low complement activation of the uncoated hydrophilic micro porous membrane according to the invention has been demonstrated before. Therefore, complement activation of the uncoated membrane was compared to the coated membrane. FIGS. 5 and 6 demonstrate that complement activation both in plasma blood out and in plasma filtrate is not negatively influenced by the coating.

Figure 7:
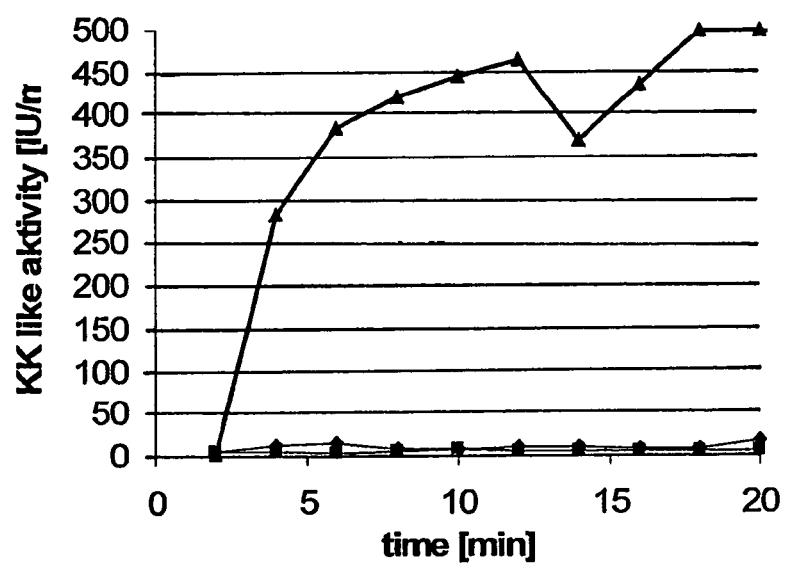
FIG. 7: Kallikrein-like activity (Kallikrein beta 2 macroglobulin complex) in plasma (blood out) during perfusion of an untreated micro-porous membrane (-■-) and a micro porous membrane treated with a 1.0 wt.-% (-♦-) Polysorbate 20. The symbol (-▲-) denotes the positive control.

Activation of the contact phase (analyzed as kallikrein-like activity (=kallikrein alpha-2-macroglobulin complex)) has been assessed during perfusion of miniaturized devices with human plasma (Example 8). The low contact phase activation of the uncoated hydrophilic micro-porous membrane according to the invention has been demonstrated before. Therefore, contact phase activation of the uncoated and the coated membrane was compared. FIG. 7 shows that contact phase activation is not negatively influenced by the coating.

In conclusion, the coated micro porous membranes showed, in vitro, an equally favourable behaviour in terms of complement activation and contact phase activation as the uncoated membrane. Regarding thrombogenicity and platelet drop, the treated membrane shows a significantly improved activation profile in comparison to the untreated membrane, which makes it more suitable, for example, for application in plasmapheresis therapies which involve re-infusion of plasma.

In case of the hydrophilic haemodialysis membrane, the thrombogenicity of the membrane is, due to the treatment with a non-ionic surfactant according to the invention, clearly improved (Example 6 and FIGS. 8 and 9).

EXAMPLES

Example 1

Preparation of a Hydrophilic Micro Porous Membrane (A) A polymer solution was prepared by dissolving 18.0 wt-% polyethersulfone (PES; BASF Ultrason 6020), 3.25 wt-% low molecular weight polyvinylpyrrolidone (PVP; BASF K30) and 8.0 wt-% high molecular weight polyvinylpyrrolidone (PVP; BASF K85 or 1(90) and 6.0 wt-% water in 70.75 wt-% N-methylpyrrolidone (NMP). The viscosity of the polymer solution at room temperature was 61810 mPa×s. To prepare the solution, NMP and the water were placed in a three neck-flask with finger-paddle agitator in the centre neck. Then, the PVP was added to the NMP and stirred at 50° C. until a homogeneous clear solution was formed. Finally, the polyethersulfone (PES) was added. The mixture was stirred at 50° C. until a clear high viscous solution is obtained. The warm solution was cooled down to 20° C. and degassed. To fully degas the solution the highly viscous polymer solution was transferred into a stable stainless steel container, the container was closed tightly and vacuum was applied to the container. The solution was degassed at 50 mmHg for 6 hours. During this degassing procedure the container was moved to create a larger surface and thinner film thickness of the polymer solution in the container to improve the degassing procedure.

To form a membrane the polymer solution was heated up to 50° C. and passed through a spinning die into a precipitation bath. As centre fluid a mixture of 25.0 wt-% water and 75.0 wt.-% NMP was used. The temperature of the die was 45° C. The hollow fibre membrane was formed at a spinning speed of 13 m/min. The liquid capillary leaving the die was passed into a heated water bath (precipitation bath) having a temperature of 85° C. Vapour created by the heat water bath surrounded the fibre. The distance between the exit of the die and the precipitation bath was 5 cm. The formed hollow fibre membrane was guided through 5 different water baths having a temperature of 65° C. Finally, the membrane was wound onto a winding-up equipment. The fibres were transferred into bundles and washed with water at 75° C. to remove traces of NMP and water soluble polymer residuals. The resulting hollow fibre membrane had an inner diameter of 328 µm, an outer diameter of 426 µm and a fully asymmetric membrane structure. The measured total protein sieving coefficient was 100% at the transmembrane pressures (TMP) of 30, 70 and 110 mmHg (Mean Blood flow QB: 4.1 ml/min, mean shear rate: 260 l/s). The degree of free haemoglobin as the corrected filtrate value (see description of methods) was below the border of starting haemolysis of 0.2 for the tested values of 30, 70 and 110 mmHg (B) In Example 1(B) the same compositions of the polymer solution and the precipitation bath were used as in Example 1(A). The viscosity of the polymer solution at room temperature was 62500 mPa×s. As centre fluid a mixture of 22.0 wt.-% water and 78.0 wt.-% NMP was used. The membrane formation procedure was the same as in Example 1 with the exceptions that the temperature of the die was 50° C., distance between the die and the precipitation bath was 8 cm, and the temperature of the precipitation bath was 50° C. Further, in addition to Example 1(A) the liquid fibre leaving the spinning die passed a spinning shaft of 6 cm length extending from the exit of the die to a distance of about 2 cm above the surface of the precipitation bath. The spinning shaft provided for a space of a conditioned atmosphere of steam or humid air surrounding the fibre when travelling from the exit of the spinning die into the precipitation bath. The steam or humid air was thereby generated by evaporation of water from the precipitation bath. In this example, no additional steam was supplied from an external source. The resulting hollow fibre membrane had an inner diameter of 318 µm, an outer diameter of 422 µm and a fully asymmetric membrane structure. The total protein sieving coefficient was 100% at transmembrane pressures (TMP) of 50, 100 and 150 mmHg (Mean Blood flow QB: 3.0 ml/min, mean shear rate: 250 l/s), respectively. Additionally, the long term stability of the total protein sieving coefficient was determined at a TMP of 50 mmHg. The total protein sieving coefficient was 100% after 15 minutes and 95 after 60 minutes. The degree of free haemoglobin as the corrected filtrate value (compare description of the method) was below the border of starting haemolysis of 0.2 for the tested value of 30 mnmHg.

Example 2

Treatment of a Hydrophilic Membrane with Polysorbate 20

A 1 wt.-% Polysorbate 20 solution is prepared by adding Polysorbate 20 to demineralised and degassed water. The mixture is stirred on a magnetic stirrer for 15 minutes. A small fraction of the resulting solution is taken for analysing the exact concentration of Polysorbate by RP-HPLC. A filter device comprising a hydrophilic micro porous hollow fiber membrane bundle prepared according to Example 1 is installed within a set-up according to FIG. 2 and filled on the blood and dialysate side with a total of 290 g of the Polysorbate 20 solution. The filling is done in a way to avoid or remove air from the device. After 30 minutes the Polysorbate 20 solution is removed from the filter and reinserted again into the system as before. Any excess solution is stored for further analysis. After 30 minutes the solution is again removed and stored for further analysis. When the solution is removed, care is taken to drain the filter long enough to avoid having more than 35 g of solution remaining in the filter. The filter is then dried with an air stream at 50° C. and a flow of 6 $Nm^3/h$ for 65 minutes. After that the filter is packed and steam sterilized according to generally known procedures.

Example 3

Quantitative Analysis of Polysorbate 20 in Aqueous Solutions

The method for quantitatively determining the amount of e.g. Polysorbate 20 in an aqueous solution is based on the acidic hydrolysis of the sorbitan laurate ester, followed by measuring the amount of the laurine acid (n-dodecane acid) by RP-HPLC. Details of quantitative determination of polysorbate 20 are provided by Ő szi and Pethő, 1998: Quantitative determination of polysorbate 20 in nasal pharmaceutical preparations by high-performance liquid chromatography. *J. Pharm. Biomed. Anal.* 18, 715-720.

A probe of 1 ml of a Polysorbate 20 solution is admixed with 1 ml 4M $H_2SO_4$. After approximately 24 hours the reaction is stopped by adding 4 ml acetonitrile. The resulting solution can be directly submitted to the RP-HPLC. The mobile phase is a 20 mM phosphate buffer in Millipore-Q-Water. pH is adjusted to 2.8 with dilute phosphoric acid. 250 ml of the buffer solution are admixed with 750 ml ACN. The flow is 1.1 ml/min. Detector: UV (210 nm). Injection volume is 200 µl; analysis time is 20 min. Temperature is room temperature.

Example 4

Quantitative Analysis of Polysorbate 20 on a Treated Membrane

The amount of polyoxyethylene sorbitan which remains on a hydrophilic membrane after said membrane has been treated with a polyoxyethylene sorbitan solution according to the invention is indirectly determined. All fractions of the initial solution which are removed from the membrane are collected and the amount of polyoxyethylene sorbitan, e.g. Polysorbate 20, in the pooled fractions is determined with the method of Example 3. The difference between the amounts of polyoxyethylene sorbitan in the solution applied for the coating procedure and in the pooled fractions is determined and will give the amount of polyoxyethylene sorbitan which remained on the membrane.

Two filters, Filter A and Filter B, comprising hydrophilic micro porous hollow fiber membranes prepared according to Example 1 were coated according to Example 2. The accessible fiber bundle exposed to the Polysorbate 20 solution had a dry weight of 9 g, respectively. The pooled fractions of the solution removed from Filter A had a Polysorbate concentration of 8.37 mg Polysorbate 20 per g solution (262 g in total); the ones from Filter B had a Polysorbate 20 concentration of 8.35 mg per g solution (262 g in total). Accordingly, 707 mg of Polysorbate 20 remained on Filter A, 712 mg Polysorbate 20 remained on Filter B. The amount of Polysorbate 20 remaining on the membrane after the treatment is 78.6 mg per unit dry weight (g) of membrane A and 79.1 mg per unit dry weight (g) of membrane B.

Example 5

Quantitative Analysis of the Amount of Polysorbate 20 Infused into a Patient in a Simulated Plasmapheresis Treatment A plasmafilter comprising a hydrophilic micro porous membrane was coated according to Example 2 and steam sterilized. In order to determine the amount of Polysorbate 20 is removed from the membrane and infused into a patient during a standard plasmapheresis treatment, such treatment was simulated. The parameters for plasmapheresis were chosen to correspond to the clinical practice (QB=150 ml/min; UF (substitution fluid)=45 ml/min; time=1 hour).

After priming the filled system had a total volume of 609 ml. During the simulated treatment the ultrafiltrate (45 ml/min) was removed and substituted with the same amount of water. At the end of the simulated treatment the total filtrate (2700 ml) was analysed. It contained a total amount of 13.88 mg Polysorbate 20. The remaining pool of 609 ml was also analysed at the end of the treatment, showing a Polysorbate 20 concentration below the limit of detection (0.4 mg/ml).

The Experiment shows that the amount of Polysorbate 20 released during a standard treatment is neglectable. For comparison, an ADI (Acceptable Daily Intake) of 10 mg/kg body weight was established for Polysorbate 20 by the FAO/WHO Expert Committee on Food Additives.

Example 6

Thrombogenicity and Platelet Drop

Thrombin-Antithrombin III (TAT) levels are measured and platelet counts are done after passage of heparinised fresh human platelet rich plasma (PRP) along the hydrophilic micro porous membrane, through the membrane and in the pool as a marker for thrombogenicity. The experiment is carried out in a recirculating modus, as a high volume of plasma is required to test in the "single pass modus". During 45 minutes at 37° C. of perfusion samples are taken continuously.

In case of a hydrophilic semipermeable membrane for haemodialysis Thrombin-Antithrombin III (TAT) levels are measured and platelet counts are done after passage of heparinised fresh human platelet rich plasma (PRP) through the miniaturized dialyzer as a marker for thrombogenicity. The experiment was performed recirculating at 37° C. for 45 minutes and samples were taken continuously.

Thrombin-Antithrombin III as a marker for thrombogenicity was analyzed with a TAT-Elisa test kit from Behring, Germany. Additional to the TAT analysis, cell numbers (platelets) were analyzed during the perfusion with a cell counter (Sysmex KX-21, Germany).

Example 7

Complement Activation

Complement activation, as generated by the terminal complement complex (TCC), is measured in vitro before and after the passage of fresh heparinised human plasma through the minimodule. Additionally, the generation of TCC in the filtrate is measured for tests with the hydrophilic, micro porous membrane. The experiment is carried out in a single pass modus at 37° C. during 30 minutes. Cuprophan® was used as a positive control. TCC as a marker of complement activation was analyzed with an Elisa test system. Details of complement activation measurement are as described by Deppisch et al, 1990: Fluid Phase Generation of Terminal Complement Complex as a Novel Index of Biocompatibility. *Kidney International* 37, 696-706.

Example 8

Contact Phase Activation

Kallikrein like activity (kallikrein alpha 2 macroglobulin complex) as marker for contact phase activation is measured after passage of citrated human platelet poor plasma (PPP) along the hydrophilic micro porous membrane, through the membrane and in the pool. The experiment is carried out in a single pass modus during 20 minutes at 37° C. using roller pumps. The samples were analyzed photometrically at 405 nm.

The invention claimed is:

1. A hydrophilic membrane for medical use, comprising: one of polysulfone, polyethersulfone and polyarylethersulfone; and
polyvinylpyrrolidone as main structural components; and a non-ionic surfactant in an amount of from 1 mg to 200 mg per gram dry weight of the hydrophilic membrane.

2. A hydrophilic membrane according to claim 1, wherein the non-ionic surfactant is a polyoxyethylene sorbitan.

3. A hydrophilic membrane according to claim 1, wherein the polyoxyethylene sorbitan is at least one member selected from the group consisting of: polyoxyethylene sorbitan acyl ester, polyoxyethylene sorbitan monolaurate, polyoxyethylene sorbitan monopalmitate, polyoxyethylene sorbitan monostearate, polyoxyethylene sorbitan tristearate and polyoxyethylene sorbitan monooleate.

4. A hydrophilic membrane according to claim 3, wherein the polyoxyethylene sorbitan is polyoxyethylene sorbitan monolaurate.

5. A hydrophilic membrane according to claim 1, wherein the non-ionic surfactant is present in or on the membrane in an amount of from 50 mg to 100 mg per gram dry weight of the hydrophilic membrane.

6. A hydrophilic membrane according to claim 1, wherein the membrane is a micro-porous membrane.

7. A hydrophilic membrane according to claim 1, wherein the membrane is a semipermeable separation membrane.

8. A hydrophilic membrane according to claim 1, wherein the membrane is a hollow fiber membrane.

9. A process for adsorbing a non-ionic surfactant to a hydrophilic membrane comprising: providing a solution of a non-ionic surfactant in water; contacting the hydrophilic membrane with the solution by applying the solution to the hydrophilic membrane; removing the solution from the membrane, wherein the amount of solution remaining on the membrane should not exceed 25% of the total amount of solution applied to the membrane; and drying the membrane.

10. A process according to claim 9, wherein the membrane is rinsed after removing the solution from the membrane, with a solution capable of dissolving the non-ionic surfactant, said solution comprising water and aqueous solutions of electrolytes.

11. A process according to claim 9, wherein the non-ionic surfactant is a polyoxyethylene sorbitan.

12. A process according to claim 9, wherein the membrane is treated within a housing.

13. A process according to claim 9, wherein the membrane is sterilized by steam sterilization, ETO sterilization, or by both steam sterilization and ETO sterilization.

14. A process according to claim 9, wherein the solution of a non-ionic surfactant in water comprises from 0.05 wt.-% to 20 wt.-% polyoxyethylene sorbitan.

15. A process according to claim 9, wherein the membrane is contacted with the solution for from 1 minute to 2 hours at temperatures from 4° C. to 60° C.

16. A process according to claim 9, wherein the solution is circulated when applied to the membrane in order to contact said membrane.

17. A process according to claim 10, wherein the at least one aqueous solution of electrolytes comprises saline buffer solutions, alcohols, organic solvents, or mixtures thereof.

* * * * *

UNITED STATES PATENT AND TRADEMARK OFFICE
CERTIFICATE OF CORRECTION

PATENT NO. : 8,528,744 B2  Page 1 of 1
APPLICATION NO. : 12/680531
DATED : September 10, 2013
INVENTOR(S) : Krause et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 550 days.

Signed and Sealed this
Fifteenth Day of September, 2015

Michelle K. Lee
*Director of the United States Patent and Trademark Office*